United States Patent [19]  [11]  4,376,769
Sherlock Margaret H.  [45]  Mar. 15, 1983

[54] SUBSTITUTED IMIDAZO THIAZOLES THIAZINES, THIAZEPINES AND THIAZOCINES

[75] Inventor: Sherlock Margaret H., Bloomfield

[73] Assignee: Schering Corporation, Kenilworth, N.J.

[21] Appl. No.: 275,166

[22] Filed: Jun. 19, 1981

[51] Int. Cl.³ .................. A61K 31/425; A61K 31/54; C07D 513/04

[52] U.S. Cl. .................. 424/246; 260/245.6; 424/270; 424/273 R; 544/48; 546/271; 548/154; 548/155

[58] Field of Search .................. 548/154, 155; 544/48; 546/271; 260/245.6; 424/246, 270, 273 R

[56] References Cited

U.S. PATENT DOCUMENTS

| | | | |
|---|---|---|---|
| 3,274,209 | 9/1966 | Ralymaekers et al. | 260/306.7 |
| 3,463,786 | 8/1969 | Bullock | 260/306.7 |
| 3,547,996 | 12/1970 | Bullock | 548/154 X |
| 4,025,625 | 5/1977 | Rooney et al. | 544/48 |
| 4,059,588 | 11/1977 | Baklien et al. | 548/155 |
| 4,150,141 | 4/1979 | Berger | 424/270 |

FOREIGN PATENT DOCUMENTS 353 1/1979 European Pat. Off. .

OTHER PUBLICATIONS

Bayles et al., Tetrahedron Letter, No. 51 (1975) pp. 4587–4590.
Okada et al., J. Org. Chem., vol. 42, No. 15 (1977) pp. 2594–2597.

*Primary Examiner*—Richard Raymond
*Attorney, Agent, or Firm*—Gerald F. Swiss; Gerald S. Rosen; Bruce M. Eisen

[57] ABSTRACT

Disclosed herein are novel tetrahydro imidazo thiazoles, tetrahydro imidazo thiazines, hexahydro imidazo thiazepines and hexahydro imidazo thiazocines, intermediates for the preparation thereof, methods of using the compounds as anti-inflammatory agents and methods of using an intermediate thereof as anti-secretory agents to relieve the symptoms of gastric distress.

15 Claims, No Drawings

SUBSTITUTED IMIDAZO THIAZOLES THIAZINES, THIAZEPINES AND THIAZOCINES

This invention relates to 2,3,5,6 tetrahydroimidazo thiazoles; 2,3,6,7-substituted tetrahydroimidazo thiazines; 2,3,5,6,7,8 hexahydrothiazepines and 2,3,6,7,8,9 hexahydroimidazo thiazocines.

More particularly, this invention relates to compounds of the formula

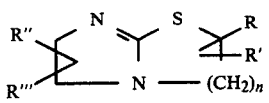

novel intermediates for the preparation thereof, and to methods for their use as anti-inflammatory agents.

In particular, the compounds of this invention may be depicted by those of the following formulae:

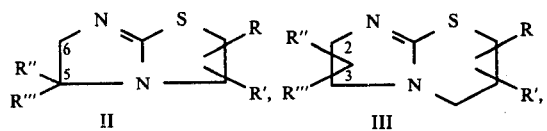

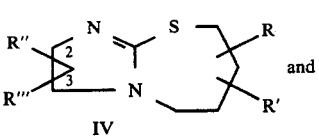

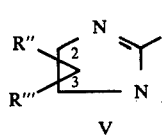

and the non-toxic therapeutically effective acid addition and quaternary salts thereof wherein R and R' independently are hydrogen and lower alkyl; R" and R'" independently are hydrogen, lower alkyl, aryl, aralkyl, pyridyl, furyl, thienyl, benzhydryl, naphthyl, indolyl, biphenyl and indenyl, including X and/or Y substituted aryl, aralkyl and pyridyl, furyl, thienyl, benzhydryl, naphthyl, indolyl, biphenyl and indenyl wherein X and Y are members of the group consisting of halogen, hydroxy, nitro, amino, lower alkyl, lower alkoxy, trifluoromethyl, trifluoromethylthio, lower alkylthio, loweralkylsulfinyl, imidazolyl, and lower alkyl sulfonyl; with the proviso that where n is 1, and one of R" or R'" is unsubstituted phenyl and R and R' are hydrogen, the other of R" and R'" must be other than hydrogen; n is an integer of 1 to 4 and with yet another proviso that when n is 1, R" and R'" must be substituents at the 5-position of the imidazolidino moiety.

Certain of the compounds of this invention exist as stereoisomers and others having a chiral center exist as optical isomers. All such compounds are embraced by this invention.

As used herein the terms alkyl and alkoxy denote such groups having 1 to 12 carbon atoms. The terms lower alkyl and lower alkoxy denotes such groups having 1 to 6 carbon atoms. The term aryl denotes phenyl, naphthyl and biphenyl and X and/or Y substituted members of this group. The term aralkyl denotes aromatic groups having 7 to 18 carbon atoms, preferably from 7 to 12 carbon atoms. Exemplary of aralkyl groups are benzyl, phenylethyl and the like. The term heteroaryl when used herein denotes heterocycle aromatic groups such as indolyl, benzofuryl, benzothienyl and the 5 or 6 membered ring heterocycles such as pyridyl, pyranyl, furyl, thienyl, pyrimidyl, pyrazinyl and the like.

SUMMARY AND DETAILED DESCRIPTION OF THE INVENTION

The compounds of this invention may be prepared according to the following flow diagram by employing a suitably substituted aldehyde or ketone. It is to be noted that the substituted aldehyde or ketone become the R" and/or the R'" substituent of compound I. X and Y are as previously defined.

The monoaryl compounds of this invention may be prepared as follows:

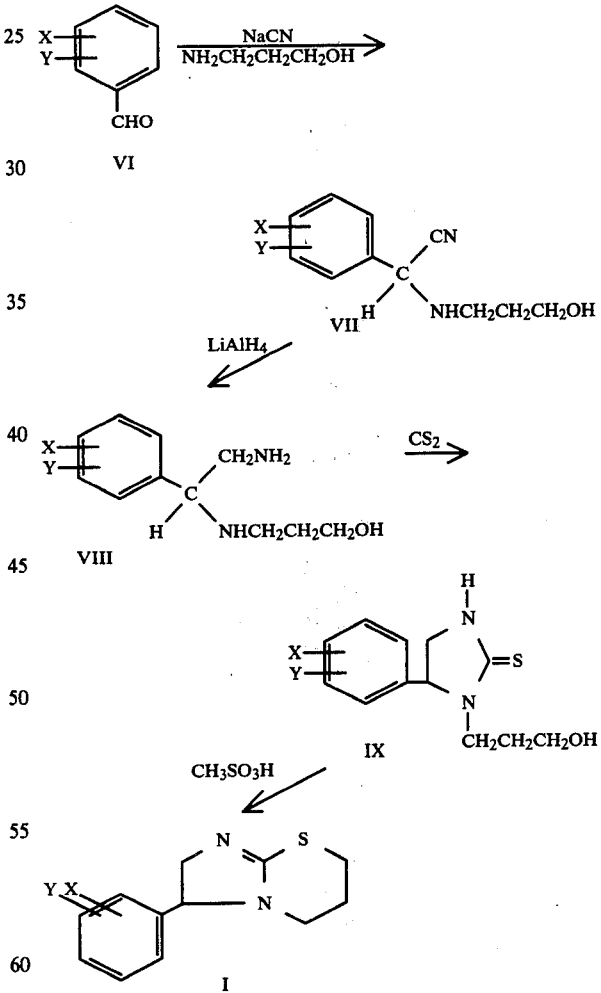

Gem diaryl compounds of this invention may be prepared as follows. This procedure is also effective for producing aryl-alkyl compounds of this invention wherein both groups are substituents on the same carbon atom.

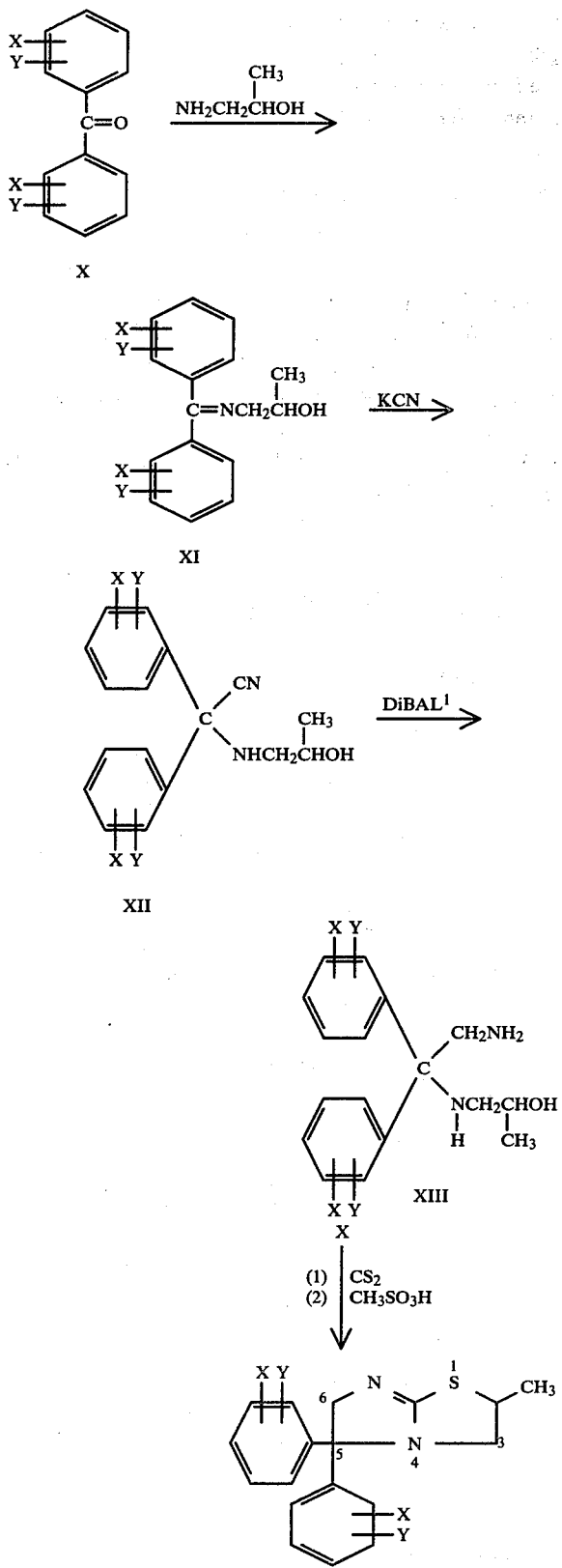

[1]Di-isobutyl aluminum hydride wherein X and Y are as previously defined and R is methyl.

In the foregoing flow diagrams, the preparation of a 3-monoaryl imidazothiazine and a 5,5-diaryl imidazothiazole are depicted.

Compounds having 7 and 8 membered rings (i.e. imidazo thiazepines and imidazo thiazocines) may be prepared by reacting the appropriate omega amino alkyl carbinol with an appropriately substituted aldehyde or ketone. By the term omega amino alkyl carbinol is meant that the amino group and the hydroxyl group are at opposite ends of the alkyl chain. Branched chain alkyl groups may be used to prepare compounds having R and/or R'-substituents as shown by the flow diagram depicting the preparation of a gem diaryl compound wherein R is methyl.

EXAMPLE 1

3-(4-Fluorophenyl)2,3,6,7-tetrahydro-5H-imidazo[2,1-b][1,3]thiazine (A) 4-Fluoro-α-[(3-hydroxypropyl)amino]benzeneacetonitrile to a cold solution (0° C.) of 30.2 g. of 3-amino-1-propanol dissolved in 161.2 ml of 2.5 N hydrochloric acid, add 19.8 g of sodium cyanide followed by a solution of 50.0 g of 4-fluorobenzaldehyde in 160 ml of methanol. Stir the reaction mixture at room temperature (20° C.) for twenty four (24) hours, then treat with 500 ml of water and extract with ethyl ether. Dry the ether extract over sodium sulfate and concentrate to an oily residue which subsequently crystallizes. Recrystallize from isopropyl ether to obtain thereby the title compound which melts at 69°–70° C.

(B) 3-[(2-Amino-1-(4-fluorophenyl)ethyl)amino]-1-propanol

Prepare a suspension of lithium aluminum hydride in 1.0 liter of cold (−10° C.) ethyl ether with stirring. Add to the suspension a solution of 50 g of 4-fluoro-α-[(3-hydroxypropyl)amino]benzeneacetonitrile in 500 ml of ether and 100 ml of tetrahydrofuran under nitrogen. Stir the reaction mixture for five (5) hours at 0° C. then overnight at room temperature. Cool the reaction mixture to 0° C. and treat dropwise with 38 ml of water followed by 38 ml of 15% sodium hydroxide solution and 70 ml of water. Stir the reaction mixture for one-half hour, filter and concentrate to a solid. Extract the filter cake with methylene chloride several times and concentrate the filtrate to a residue. Crystallize the residues from isopropyl ether to obtain thereby the title product melting 110°–112° C.

(C) 5-(4-Fluorophenyl)-1-(3-hydroxypropyl)imidazolidine-2-thione

Dissolve 5.3 g of the product of Step B in 50 ml of 80% aqueous ethanol, then add 2.02 g of carbon disulfide and reflux the mixture for one (1) hour. Cool the solution then treat with 0.2 ml of concentrated hydrochloric acid and reflux the mixture for sixteen (16) hours. Concentrate the reaction mixture in vacuo, extract with methylene chloride and dry the extract. Concentrate the extract to a residue and triturate with isopropyl ether to obtain the product of this step. Yield 5.2 g M.P. 104°–106° C. Recrystallize the product from ethanol petroleum ether to obtain the product as a colorless solid. M.P. 105°–106°.

(D) 3-(4-Fluorophenyl)2,3,6,7-tetrahydro-5H-imidazo[2,1-b][1,3]thiazine

Dissolve 4.9 g of the product of Step C in 30 ml of 1,2-dichloroethane and 5.6 g of methane sulfonic acid (98%). Reflux the mixture for one (1) hour then remove the solvent in vacuo. Add 80 ml of ice-water then adjust to an alkaline pH with 10% sodium hydroxide solution. Extract with methylene chloride, dry the extract over sodium sulfate and concentrate to an oil which crystallizes from petroleum ether M.P. 69°–71° C.

SALT FORMATION

Dissolve the product (free base) of Step D in methanolic hydrogen chloride to obtain the hydrochloride salt which may be recrystallized from ethanol-ethyl acetate, M.P. 219°–220° C.

In a similar manner, salts of the other compounds of this invention may be prepared. The salts contemplated herein are those of pharmaceutically acceptable organic and inorganic acids generally used in the art such as sulfuric, hydrochloric, phosphoric, acetic, propionic, maleic, citric, oxalic, benzoic, phenylacetic, adamantane carboxylic acid and the like.

Also contemplated are quaternary salts which are prepared by the action of an alkyl halide or a dialkyl sulfate on the fused bicyclic compounds of this invention. Alternatively, the quaternary salts may be prepared by other means known in the art.

EXAMPLE 2

5,5-Diphenyl-2-Methyl-2,3,5,6-tetrahydroimidazo [2,1-b]Thiazole (A) 1-[(Diphenylmethylene)amino]Propanol-2

Dissolve 54.6 g of benzophenone, 45 g of 1-aminopropanol-2 and a pinch of p-toluene sulfonic acid in 100 ml of benzene. Heat the reaction mixture to reflux using a condenser having a Dean Stark trap. Reflux the mixture for 24 hours then concentrate the reaction mixture to a residue in vacuo. Fractionate the residue at 0.5 mm; B.P. 154°–158° C., $ND^{25°}$ 1.5875.

(B) α-Phenyl-α[(2-hydroxypropyl)amino]benzeneacetonitrile

Cool 69.0 g of 1-[(diphenylmethylene)amino] propanol-2 to 0° C. in 150 ml of absolute ethanol with stirring, add 22.0 g of potassium cyanide followed by the dropwise addition of 17.4 g of glacial acetic acid in 20 ml of ethanol. Stir the reaction mixture at 0° C. for two hours and at room temperature overnight. Pour the reaction mixture into ice water, filter the precipitate and air dry. Crystallize the crude product from a methylene chloride-petroleum ether-ethyl ether mixture to obtain thereby a colorless product M.P. 109°–111° C. (dec).

(C) 1-[(2-Amino-1,1-diphenylethyl)amino]-Propanol-2

Suspend 63 g of the product of Step B in 1.5 liters of dry toluene, cool to −5° C. Add dropwise 700 ml of diisobutyl aluminum hydride (Dibal) (20% in hexane 0.67 mole) over a one hour period in a nitrogen atmosphere. Maintain the reaction mixture at 0° C. for two hours with stirring and overnight at room temperature with stirring. Cool the reaction mixture to −5° C. and treat dropwise with 100 ml of methyl alcohol followed by 80 ml of water. Filter the reaction mixture, wash the filter cake with 4×50 ml of toluene and concentrate the filtrate and washes in vacuo to a viscous oil. Crystallize the product from 250 ml of isopropyl ether to obtain thereby the product of this Step, M.P. 97°–99° C.

(D) Repeat the procedure of Step C, Example 1 to obtain thereby 5,5-diphenyl-1-(2-hydroxypropyl)imidazolidine-2-thione.

Repeat the procedure of Step D, Example 1 with the product obtained in Step D to obtain thereby 5,5-diphenyl-2-methyl-2,3,5,6-tetrahydroimidazo [2,1-b]thiazole.

2,2-Diphenyl-2,3,6,7-tetrahydro-5H-imidazo[2,1-b][1,3]thiazine and 3,3-Diphenyl-2,3,6,7-tetrahydro-5H-imidazo[2,1-b][1,3]thiazine Suspend 10.5 g of sodium hydride (50% in mineral oil) in 100 ml of dry tetrahydrofuran and add dropwise with stirring a solution of 24 g of 5,5-diphenyl-1-(3-hydroxypropyl)imidazolidine-2-thione in 500 ml of tetrahydrofuran. Stir the reaction mixture for one hour at room temperature then add a solution of 20.2 g of 1,3-dibromopropane dropwise over a one half hour interval. Reflux the mixture for twenty hours with stirring. Cool the reaction medium, pour into 100 g of ice and filter. Concentrate the filtrate in vacuo to a residue. Triturate the residue with 600 ml of ethyl acetate to obtain thereby 14.0 g of 2,2-diphenyl-2,3,6,7-tetrahydro-5H-imidazo[2,1-b][1,3]thiazine, M.P. 184.5°–185° after recrystallization from ethyl acetate.

The ethyl acetate mother liquors are concentrated and the residue purified by high pressure liquid chromatography to obtain thereby 3,3-diphenyl-2,3,6,7-tetrahydro-5H-imidazo[2,1-b]-[1,3]thiazine, M.P. 155°–156° C.

In similar manner, by substituting an equivalent quantity of 1,4-dibromopropane in the alkylation procedure there is produced the corresponding diphenyl thiazepine, the 2,2-diphenyl analog M.P. 131°–132° C. and the 3,3-diphenyl analog M.P. 150°–151° C.

The foregoing Examples illustrate the processes whereby the compounds of this invention may be prepared.

In order to further describe the compound aspect of this invention, we have set forth below representative aldehydes and ketones which may be utilized to prepare the compounds of this invention. It is to be noted that the choice of aldehyde or ketone is determinant of the R″ and/or R‴ substituents on the imidazolidino moiety. Suitable aldehydes and ketones are set forth in the following list. These aldehydes and ketones are set forth for exemplification and are not to be construed as limiting the scope of this invention.

benzaldehyde,
2-fluorobenzaldehyde,
3-fluorobenzaldehyde
4-chlorobenzaldehyde,
2-methylbenzaldehyde,
4-methylbenzaldehyde,
3-trifluoromethylbenzaldehyde,
1,1-biphenyl-4-carboxaldehyde,
2-naphthylaldehyde,
6-methoxy-2-naphthaldehyde,
1,1-biphenylacetaldehyde,
2-methyl-3-chlorobenzaldehyde,
4-trifluoromethylbenzaldehyde, and benzene acetaldehyde,
4-pyridylaldehyde,
2,4-difluorobenzaldehyde,
3,4-dimethylbenzaldehyde,
3,4-ditrifluoromethylbenzaldehyde,
2,4-dimethylbenzaldehyde,
3,4-dichlorobenzaldehyde,
2,3-dimethoxybenzaldehyde,
4-methylthiobenzaldehyde,
4-methylsulfinylbenzaldehyde,
diphenylacetaldehyde acetophenone,
4-fluoroacetophenone,
1-phenyl-2-propanone,
1-(4-imidazo-1-yl)phenylethanone,
1-phenyl-1-pentanone,
diphenyl methanone
(4-chlorophenyl)phenyl methanone,
phenyl-2-pyridyl methanone,
phenyl-3-pyridyl methanone,
phenyl-4-pyridyl methanone,
4,4'-dichlorodiphenyl methanone,
(3-fluorophenyl)phenyl methanone, The flow diagrams set forth above and specific examples teach that the process aspect of this invention involves the formation of essentially three classes of intermediates. The first class are the nitriles whose general formula may be represented as follows:

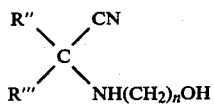

wherein n is 2, 3 or 4 and R'', R''' are as defined above when n is 3, R''=phenyl, R'''=H 2-[(3-hydroxypropyl-)amino] Benzene acetonitrile is produced, the ultimate product therefrom being a R'',R'''-substituted tetrahydroimidazothiazine. The second class of intermediates may be represented by the following general formula:

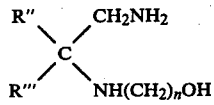

wherein R'', R''' and n are as previously defined exemplary of such intermediates are compounds VIII and XIII of the flow diagrams. The third class of intermediates may be represented by the following general formula:

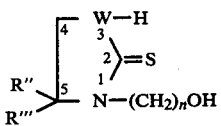

wherein R', R''' and n are as previously defined. Exemplary of such intermediates are compounds IX and the flow diagram and the product of step C of Example 1.

By selecting an appropriately substituted aldehyde or ketone such as those set forth above and by following the procedure of the foregoing Examples, the following compounds may be prepared.

5-phenyl-5-(2-pyridyl)-2,3,5,6-tetrahydroimidazo[2,1-b]thiazole,
5-phenyl-5-(3-pyridyl)-2,3,5,6-tetrahydroimidazo[2,1-b]thiazole,
5-(diphenylmethyl)-2,3,5,6-tetrahydroimidazo[2,1-b]thiazole,
5-methyl-5-phenyl-2,3,5,6-tetrahydroimidazo[2,1-b]thiazole,
5-(4-fluorophenyl)-2,3,5,6-tetrahydroimidazo[2,1-b]thiazole,
5-phenyl-5-(3-trifluoromethylphenyl)-2,3,5,6-tetrahydroimidazo[2,1-b]thiazole,
5-(4-chlorophenyl)-5-phenyl-2,3,5,6-tetrahydroimidazo[2,1-b]thiazole,
5-(4-fluorophenyl)-5-phenyl-2,3,5,6-tetrahydroimidazo[2,1-b]thiazole,
5,5-di-(4-fluorophenyl)-2,3,5,6-tetrahydroimidazo[2,1-b]thiazole,
5,5-di-(4-methylphenyl)-2,3,5,6-tetrahydroimidazo[2,1-b]thiazole,
5,5-di-(4-methoxyphenyl)-2,3,5,6-tetrahydroimidazo[2,1-b]thiazole,
5-(4-methoxyphenyl)-5-phenyl-2,3,5,6-tetrahydroimidazo[2,1-b]thiazole,
5-phenyl-3,3-dimethyl-2,3,5,6-tetrahydromidazo[2,1-b]thiazole
3,3-diphenyl-2,3,5,6,7,8-hexahydroimidazo[2,1-b][1,3]thiazepine,
3-(4-fluorophenyl)-2,3,5,6,7,8-hexahydroimidazo[2,1-b][1,3]thiazepine,
2,2-diphenyl-2,3,5,6,7,8-hexahydroimidazo[2,1-b][1,3]thiazepine,
3-(4-fluorophenyl)-3-phenyl-2,3,6,7-tetrahydro-5H-imidazo[2,1-b][1,3]thiazine,
3-(1-phenylethyl)-2,3,6,7-tetrahydro-5H-imidazo[2,1-b][1,3]thiazine,
3-(4-methylphenyl)-2,3,6,7-tetrahydro-5H-imidazo[2,1-b][1,3]thiazine,
3-(2-methylphenyl)-2,3,6,7-tetrahydro-5H-imidazo[2,1-b][1,3]thiazine,
3-(4-chlorophenyl)-2,3,6,7-tetrahydro-5H-imidazo[2,1-b][1,3]thiazine,
3-(3-fluorophenyl)-2,3,6,7-tetrahydro-5H-imidazo[2,1-b][1,3]thiazine,
3-(2-fluorophenyl)-2,3,6,7-tetrahydro-5H-imidazo[2,1-b][1,3]thiazine,
3-(4-fluorophenyl)-2,3,6,7-tetrahydro-5H-imidazo[2,1-b][1,3]thiazine,
2-phenyl-2,3,6,7-tetrahydro-5H-imidazo[2,1-b][1,3]thiazine,
3-phenyl-2,3,6,7-tetrahydro-5H-imidazo[2,1-b][1,3]thiazine,
3-(4-methylthiophenyl)-2,3,,6,7-tetrahydro-5H-imidazo[2,1-b][1,3,]thiazine,
3-(3-trifluoromethylphenyl)-2,3,6,7-tetrahydro-5H-imidazo[2,1-b][1,3]thiazine,
3-(1,1-biphenyl-4-yl)-2,3,6,7-tetrahydro-5H-imidazo[2,1-b][1,3]thiazine,
3-(2-naphthyl)-2,3,6,7-tetrahydro-5H-imidazo[2,1-b][1,3]thiazine,
3-[2-(6-methoxynaphthyl)]-2,3,6,7-tetrahydro-5H-imidazo[2,1-b][1,3]thiazine,
3-(diphenylmethyl)-2,3,6,7-tetrahydro-5H-imidazo[2,1-b][1,3]thiazine,
3-methyl-3-phenyl-2,3,6,7-tetrahydro-5H-imidazo[2,1-b][1,3]thiazine,
3,3-diphenyl-2,3,6,7-tetrahydro-5H-imidazo[2,1-b][1,3]thiazine,
2,2-diphenyl-2,3,6,7-tetrahydro-5H-imidazo[2,1-b][1,3]thiazine,
3-(4-chlorophenyl)-3-phenyl-2,3,6,7-tetrahydro-5H-imidazo[2,1-b][1,3]thiazine,
2,2-[di-(4-methylphenyl)]-2,3,6,7-tetrahydro-5H-imidazo[2,1-b][1,3]thiazine,
2,2-[di(4-fluorophenyl)]-2,3,,6,7-tetrahydro-5H-imidazo[2,1-b][1,3,]thiazine,
3-(3-pyridyl)-2,3,6,7-tetrahydro-5H-imidazo[2,1-b][1,3]thiazine,
3-(2-methyl-3-chlorophenyl)-2,3,6,7-tetrahydro-5H-imidazo[2,1-b][1,3]thiazine, Certain of the classes of intermediates for the preparation of the ultimate compounds of this invention are themselves novel and some also exhibit beneficial pharmacological properties of their own. For example, the 1-hydroxyalkyl-5-substituted imidazolidine-2-thiones (one of which is depicted as compound IX above) are active as anti-secretory agents which relieve the symptoms of gastric and duodenal ulcers.

Exemplary of such intermediates are the following which are not to be construed as limiting the scope of such compounds.

1-(3-hydroxypropyl)-5-(1-phenylethyl)imidazolidine-2-thione,
1-(3-hydroxypropyl)-5-(3-chloro-2-methylphenyl)imidazolidine-2-thione,
1-(2-hydroxyethyl)-5-(1-phenylethyl)imidazolidine-2-thione,
1-(2-hydroxypropyl)-5-(4-methoxyphenyl)imidazolidine-2-thione,
1-(2-hydroxy-2-methylpropyl)-5,5-diphenyl)imidazolidine-2-thione,
1-(3-hydroxypropyl)-5-(4-fluorophenyl)imidazolidine-2-thione,
1-(2-hydroxyethyl)-5,5-(diphenyl)imidazolidine-2-thione,
1-(3-hydroxypropyl)-5-(2-fluorophenyl)imidazolidine-2-thione,
1-(3-hydroxypropyl)-5-(3-fluorophenyl)imidazolidine-2thione,
1-(3-hydroxypropyl)-5-(4-chlorophenyl)imidazolidine-2-thione,
1-(3-hydroxypropyl)-5-(3-chloro-2-methylphenyl)imidazolidine-2-thione,
1-(2-hydroxyethyl)-5-(4-chlorophenyl)5-phenylimidazolidine-2-thione,
1-(2-hydroxypropyl)-5,5-diphenyl-imidazolidine-2-thione,
1-(2-hydroxyethyl)-5-(4-fluorophenyl)-5-phenylimidazolidine-2-thione,
1-(3-hydroxypropyl)-5-(4-chlorophenyl)-5-phenylimidazolidine-2-thione,
1-(2-hydroxyethyl)-5-(3-trifluoromethylphenyl)-5-phenylimidazolidine-2-thione,
1-(3-hydroxypropyl)-5-(4-fluorophenyl)-5-methylimidazolidine-2-thione,
1-(3-hydroxypropyl)-5-(diphenylmethyl)imidazolidine-2-thione,
1-(2-hydroxyethyl)-5-(1-phenylethyl)imidazolidine-2-thione,
1-(3-hydroxypropyl)-5-(1-phenylethyl)imidazolidine-2-thione,
1-(2-hydroxyethyl)-5-(3-pyridyl)-5-phenyl-imidazolidine-2-thione,
1-(3-hydroxypropyl)-5-phenyl-imidazolidine-2-thione,
1-(3-hydroxypropyl)-5-(6-methoxy-2-naphthyl)imidazolidine-2-thione,
1-(3-hydroxypropyl)-5-(2-methylphenyl-imidazolidine-2-thione,
1-(3-hydroxypropyl)-5-(4-methylthiophenyl)-imidazolidine-2-thione,
1-(3-hydroxypropyl)-5-(1,1'-biphenyl-4-yl)-imidazolidine-2-thione, and
1-(3-hydroxypropyl)-5-(2-naphthyl)imidazolidine-2-thione.

The foregoing compounds have utility as intermediates for the final compounds of this invention and also exhibit a pharmacological utility of their own. Thus, these compounds being anti-secretory agents capable of relieving the symptoms of gastric distress. When used for this purpose the imidazolidine-2-thiones are administered at about 10 to about 100 mpk, preferably in divided doses three to four times a day. These compounds may be prepared in the form of tablets, capsules, syrups and emulsions for oral administration. They may be admixed with the conventional excipients including but not limited to organic, or inorganic solids and the same excipients, carriers, diluents, preservatives set forth below for the anti-inflammatory products of this invention.

RESOLUTION OF
3[(2-amino-1-phenylethyl)amino]-1-propanol

Prepare a solution of 42 g of (−)dibenzoyl-1-tartaric acid monohydrate in 600 ml of absolute ethanol with warming. Add a solution of 11 g of 3[(2-amino-1-phenylethyl)amino]-1-propanol in 175 ml of absolute ethanol. Allow the resulting solution to stand at room temperature overnite and filter the colorless salt. Recrystallize the salt from 80% aqueous ethanol to obtain thereby a product melting 170°–171° C., $[\alpha]D^{26°}=(-)30.7°$ (C=1.0, dimethylformamide).

Treat the salt with concentrated aqueous sodium hydroxide solution and obtain thereby the optically active diamine, M.P. 107°–109° C., $[\alpha]D^{26°}=(-)50.6°$ (C=1.0, ethanol).

Concentrate the mother liquors of the above resolution and treat with alkali to obtain thereby the other optical enantiomer, M.P. 106°–108° C., $[\alpha]D^{26°}=(+)53.6°$ (C=1.0, ethanol).

Reaction of the (−) enantiomer with carbon disulfide yields the optically active imidazolidine 2-thione, M.P. 96°–97°, $[\alpha]D^{26°}=(+)8.3°$ (C=1.0, ethanol).

In like manner, reaction of the (+) enantiomer with carbon disulfide yields the other optically active imidazolidine 2-thione, M.P. 109°–110° $[\alpha]D^{26°}=(-)6.4°$ (C=1.0, ethanol).

Treat each of the optical isomers of the imidazolidine 2-thiones with methanesulfonic acid in the above-described manner to obtain thereby the two enantiomers of 3-phenyl-2,3,6,7-tetrahydro-5H-imidazo[2,1-b][1,3]thiazine.

The (+) rotating imidazolidine 2-thione gives the (−) rotating thiazine M.P. 71°–73° C., $[\alpha]D^{26°}(-)268.3°$ (C=1.0, ethanol). The oxalate salt M.P. 119°–121° C., $[\alpha]D^{26°}=(-)37.5°$ (C=1.0, H$_2$O).

The (−) rotating imidazolidine 2-thione gives the (+) rotating thiazine, M.P. 70°–73° C., $[\alpha]D^{26°}=(+)272.9°$ (C=1.0, ethanol). The oxalate salt, M.P. 119°–121° C., $[\alpha]D^{26°}=(+)37.8°$ (C=1.0, H$_2$O).

RESOLUTION OF
3-[(2-amino-1-(4-fluorophenyl)ethyl)amino]-1-propanol

Repeat the procedure set forth above using an equivalent quantity of 3-[(2-amino-1-(4-fluorophenyl)ethyl)amino]-1-propanol to obtain the (−)-dibenzoyl-1-tartrate salt M.P. 172°–174°, $[\alpha]D^{26°}=(-)83.4°$ (C=1.0, H$_2$O).

Treat the salt with aqueous sodium hydroxide as described above to obtain the (+) enantiomer M.P. 125°–128° C., $[\alpha]D^{26°}=(+)45.9°$ (C=1.0, ethanol)
(−) enantiomer M.P. 128°–130° C., $[\alpha]D^{26°}=(-)49.9°$ (C=1.0, ethanol)

Treat the respective enantiomers with carbon disulfide in the usual manner, the (−) enantiomer yields the imidazolidine-2-thione, M.P. 132°–133° C., $[\alpha]D^{26°} = (+)7.0°$ (C=1.0, ethanol); and the (+) enantiomer yields the imidazolidine-2-thione M.P. 131°-133° C., $[\alpha]D^{26°} = (-)6.2°$ (C=1.0, ethanol).

Treat the respective imidazolidine-2-thione enantiomers with methanesulfonic acid as described above to obtain thereby the respective optically active 3-(4-fluorophenyl)2,3,6,7-tetrahydro-5H-imidazo[2,1-b][1,3]thiazines.

As in the foregoing resolution, the (+) enantiomer of the imidazolidine2-thione produces the (−) enantiomer of the thiazine, M.P. 116°-118°, $[\alpha]D^{26°} = (-)253.2°$ (C=1.0, ethanol); hydrochloride salt, M.P. 178°-180° C., $[\alpha]D = (-) 36.6°$ (C=1.0,H$_2$O).

The (−) rotating imidazolidine -2-thione yields the (+) enantiomer of the thiazine, M.P. 110°-115° C., $[\alpha]D$ (+) 232.0° (C=1.0, ethanol) hydrochloride salt, M.P. 175°-176° C., $[\alpha]D = (+) 35.2°$ (C=1.0,H$_2$O).

The compounds of this invention including the pharmaceutically acceptable acid addition salts are potent anti-inflammatory agents. They are especially useful in the treatment of chronic inflammatory conditions such as arthritis, bursitis and rheumatism.

The anti-inflammatory potential of the compounds may be determined by the Reversed Passive Arthus Response technique as set forth below using male Wistar/Lewis inbred albino rats (Charles River) weighing 180–200 grams. The potency of the compounds is determined using indomethacin as the standard. On the basis of the test results, a dosage range of 0.25 MPK to about 50 MPK in divided doses taken at about 4 hour intervals is recommended.

Of course, the dosage to be administered depends upon the particular compound used, the age and general health of the patient and the severity of the inflammatory condition. Thus, the dose ultimately decided upon must be left to the judgement of a trained health-care practitioner.

The compounds of this invention may be processed and dispensed in tablets, capsules or elixirs, for oral administration; and solutions or suspensions for parenteral administration. In whatever form the compounds are dispensed, they may be admixed with the pharmaceutically acceptable excipients, binders, dispersing agents and carriers generally used in the art.

Exemplary of the pharmaceutical carriers, excipients, preservatives and binders are gelatin, lactose, starch, magnesium stearate, talc, vegetable oils, gums, polyalkylene glycols, etc. The pharmaceutical dosage forms are prepared by the methods conventionally used in the art. Further, the dosage units may also contain a compatible anti-depressant and/or analgesics to treat the depression and pain usually associated with chronic inflammatory conditions.

Reversed Passive Arthus Response (RPAR) Animals, Materials and Methods

Male Wistar/Lewis inbred albino rats weighing 180–200 grams obtained from Charles River Breeding Laboratories are used in these experiments. The rats are housed 3 animals/cage and are fasted 24 hours prior to the study and during the study. Water is allowed ad libitum. The animals are numbered 1-3 in each cage and colored marker for identification purposes.

Drug and Reagent Preparation

All reagents and drugs are prepared just prior to the study. Crystallized and lyophylized bovine serum albumin (BSA), obtained from Sigma Chemical Company, is solubilized without shaking in cold sterile pyrogen free saline (10 mg/ml). Lyophylized anti-bovine serum albumin (IGG fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Drug Administration and Induction of Inflammation

One hour prior to sensitization with BSA groups of animals (minimum of 6/groups) are given drug in MC by gauge according to body weight (1.0 cc/100 grams). Controls are given MC alone and a drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after dosing the animals are lightly anesthetized with ether and "sensitized" by injection into the penile vein with 0.2 ml of PFS containing 1.0 mg of BSA. One hour later the animals are "challenged" in the right rear paw with subplantar injections of 0.2 ml of PFS containing 0.1 mg of anti-BSA. Immediately after the subplantar injection the right paw is dipped (up to the lateral maleolus) into the mercury well of a plethysmograph. The volume of mercury displaced is converted to weight and recorded. This value is considered to be the control reading for the animal. Paw volumes are also recorded with a plethysmograph during the development of the inflammation at 2 and 4 hours post-challenge.

Results

Results are expressed by the change in paw volume (Δ paw volume) from the control reading for each animal to that recorded 2 and 4 hours post-challenge. All drug treated groups are compared to the MC control for significant differences with an analysis of variance. Differences from control in drug-treated groups are expressed as percent change from control.

We claim:

1. Compounds of the formula

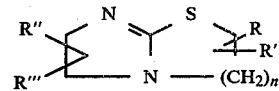

and the non-toxic therapeutically effective acid addition and quatenary salts thereof wherein R and R' are independently hydrogen and lower alkyl; R" and R'" independently are members of the group consisting of hydrogen, lower alkyl, aryl, aralkyl, pyridyl, furyl, thienyl, benzhydryl, naphthyl, indolyl, biphenyl and indenyl, including X and/or Y substituted aryl, aralkyl, pyridyl, furyl, thienyl, benzhydryl, naphthyl, indolyl, biphenyl and indenyl wherein X and Y are members of the group consisting of halogen, hydroxy, nitro, amino, lower alkyl, lower alkoxy, trifluoromethyl, imidazolyl, trifluoromethylthio, lower alkylthio, lower alkyl sulfinyl and lower alkyl sulfonyl; n is an integer of 1 to 4; with the proviso that when n is 1 R" and R'" are not hydrogen or lower alkyl and when n=2 at least one of R" and R'" cannot be hydrogen; and with the further proviso that when n is 1, R" and R'" are not both phenyl at the 6-position of the imidazoline moiety.

2. A compound of claim 1 of the formula

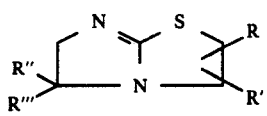

wherein R,R',R",R'" are as defined in claim 1.

3. A compound of claim 1 of the formula

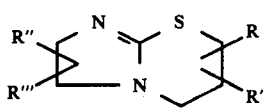

wherein R,R',R" and R'" are as defined in claim 1.

4. A compound of claim 1 of the formula

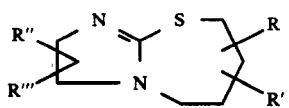

wherein R,R',R" and R'" are as defined in claim 1.

5. A compound of claim 1 of the formula

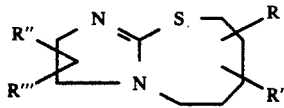

wherein R,R'R",R'" are as defined in claim 1.

6. A compound of claim 2 wherein R and R' are hydrogen, R" and R'" are selected from the group consisting of aryl, aralkyl and pyridyl.

7. A compound of claim 6 wherein R" and R'" are phenyl, said compound being 5,5-diphenyl-2,3,5,6-tetrahydroimidazo [2,1-b]thiazole.

8. A compound of claim 2 wherein R is methyl at the 2 position, R' is hydrogen, R" and R'" are phenyl, said compound being 2-methyl-5,5-diphenyl-2,3,5,6-tetrahydroimidazo [2,1-b] thiazole.

9. A compound of claim 3 wherein R and R' are hydrogen, R" and R'" are defined in claim 3.

10. A compound of claim 3 wherein R is lower alkyl, R' is hydrogen, R" and R'" are as defined in claim 3.

11. A compound of claim 9 wherein R" is halogeno substituted phenyl and R'" is hydrogen.

12. A compound of claim 11 wherein R" is 4-fluorophenyl at position 3, R'" is hydrogen, said compound being 3-(4-fluorophenyl)-2,3,6,7-tetrahydro-5H-imidazo[2,1-b] [1,3]thiazine.

13. A compound of claim 9 wherein R" is phenyl and R'" is hydrogen, said compound being 3-phenyl-2,3,6,7-tetrahydro-5H-imidazo [2,1-b] [1,3] thiazine.

14. The method of eliciting an anti-inflammatory response from a mammal suffering with an inflammatory condition which comprises administering to the mammal an anti-inflammatory quantity of a compound of the formula of claim 1.

15. A method according to claim 14, wherein the anti-inflammatory response is elicited by a member of the group consisting of 5,5-diphenyl-2,3,5,6-tetrahydroimidazo [2,1-b] thiazole; 3-(4-fluorophenyl)-2,3,6,7-tetrahydro-5H-imidazo [2,1-b][1,3] thiazine; and 3-phenyl-2,3,6,7-tetrahydro-5H-imidazo[2,1-b][1,3] thiazine, or a non toxic pharmaceutically acceptable acid addition salt thereof.

* * * * *

UNITED STATES PATENT AND TRADEMARK OFFICE
CERTIFICATE OF CORRECTION

PATENT NO. : 4,376,769

DATED : March 15, 1983

INVENTOR(S) : Margaret H. Sherlock et al

It is certified that error appears in the above-identified patent and that said Letters Patent is hereby corrected as shown below:

On the title page, Item (75) Insert

-- Sandra Sasso --.

Signed and Sealed this

Fifth Day of July 1983

[SEAL]

Attest:

Attesting Officer

GERALD J. MOSSINGHOFF

Commissioner of Patents and Trademarks